United States Patent [19]

Cray et al.

[11] Patent Number: 5,100,991

[45] Date of Patent: Mar. 31, 1992

[54] ORGANOSILICON COMPOUNDS

[75] Inventors: Stephen E. Cray; James McVie, both of South Glamorgan, Wales; Paul A. Yianni, Limal, Belgium

[73] Assignee: Dow Corning Limited, Barry, Wales

[21] Appl. No.: 690,371

[22] Filed: Dec. 10, 1990

Related U.S. Application Data

[63] Continuation of Ser. No. 353,300, May 17, 1989, abandoned.

[30] Foreign Application Priority Data

May 17, 1988 [GB] United Kingdom ............... 8811601
Feb. 9, 1989 [GB] United Kingdom ............... 8902939

[51] Int. Cl.$^5$ .............................................. C08G 77/04
[52] U.S. Cl. ........................................ 528/26; 524/838; 556/419; 528/27; 528/38
[58] Field of Search ................ 528/26, 27, 38; 556/419; 524/838

[56] References Cited

U.S. PATENT DOCUMENTS 4,104,296 8/1978 Pike ...................... 556/419
4,591,652 5/1986 DePasquale et al. ............. 556/419
4,624,794 11/1986 Cooke et al. ...................... 252/8.8

Primary Examiner—Melvyn I. Marquis
Attorney, Agent, or Firm—George A. Grindahl

[57] ABSTRACT

The specification describes and claims certain organosilicon compounds and the preparation thereof. The organosilicon compounds comprise (A) a silane according to the general formula $R^1{}_aA_bSi(R''NXR')_c$ or (B) a polysiloxane comprising one or more siloxane units according to the general formula (i)

$$R_m{}^2(R''NXR')_p SiO_{\frac{(4-(m+p))}{2}}.$$

any remaining units of the polysiloxane being at least predominantly according to the general formula (ii)

$$R_q{}^2(R''NR^4H)_r SiO_{\frac{(4-(q+r))}{2}}.$$

A represents a hydroxyl or a hydrolyzable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, $R'$ represents a group $R^4$ or a group X, R'' represents a divalent hydrocarbon group which may have nitrogen, oxygen or sulphur present in the carbon chain, X represents a group $CO(CHR)_nOH$ in which R represents a hydrogen atom or an alkyl group, a has the value 0, 1, or 2, b has the value 1, 2, or 3, c has the value 1 or 2, the sum of $a+b+c=4$, m has the value 0, 1 or 2, p has the value 1 or 2, q has the value 0, 1, 2 or 3, r has the value 0, 1 or 2, and n has a value in the range 2 to 7.

The organosilicon compounds are useful in compositions for treating fabrics. Preferred organopolysiloxanes are of the average general formula.

13 Claims, No Drawings

ORGANOSILICON COMPOUNDS

This is a continuation of copending application(s) Ser. No. 07/353,300 filed on May 17, 1989, and now abandoned.

This invention is concerned with organosilicon compounds.

Polysiloxanes are known which have substituent groups including amido groups. It is known to prepare such materials from the corresponding amino polysiloxane by reaction with an organic acid or organic acid anhydride. It has been proposed to use such materials, for example in fibre and fabric treatment. However, this type of material tends to confer a somewhat harsh handle to fabric. It has been proposed to prepare silanes having substituents which include a distally extending tail of monohydroxysubstituted carbon atoms linked to the silicon atom through an amido group, by reaction between the corresponding amino silane and an aldonic acid lactone, as exemplified by delta gluconolactone. These materials have a plurality of hydroxyl groups in the substituent. They are water soluble and are said to cure to a hard clear insoluble protective coating on certain substrates. These characteristics are undesirable for some applications; furthermore we have found such materials are prepared with difficulty.

It is an object of the present invention to provide an improved organosilicon compound containing amido groups.

The present invention provides in one of its aspects a polydiorganosiloxane having a group $=NCO(CHR)_nOH$ connected with a silicon atom of a siloxane unit of the polydiorganosiloxane wherein R represents a hydrogen atom or an alkyl group and n has a value in the range 2 to 7.

An organosilicon compound according to the invention may be for example, (A) a silane or (B) a polysiloxane. Silanes may have the formula $R_a^1A_bSi(R''NXR')_c$ and polysiloxanes may include siloxane units (i)

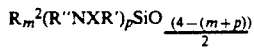

in which A represents a hydroxyl or a hydrolysable group, $R^1$ represents a monovalent hydrocarbon group having up to 8 carbon atoms, $R^2$ represents a hydroxyl group, a group $R^1$, a group $OR^1$ or a group $COR^1$, R' represents a hydrogen atom, an alkyl group having 1 to 20 carbon atoms, an alkenyl group or an aryl group, or a group X, R'' represents a divalent hydrocarbon group which may have nitrogen, oxygen or sulphur present in the carbon chain, X represents the group $CO(CHR)_nOH$, a has the value 0, 1 or 2, b has the value 1, 2 or 3, c has the value 1 or 2, the sum of $a+b+c=4$, m has the value 0, 1 or 2 and p has the value 1 or 2.

Organosilicon compounds according to the invention are materials in which the group $=NCO(CHR)_nOH$ is part of a substituent linked to the silicon, atom through a divalent linkage R''. Preferably R represents a hydrogen atom and n has the value 3, 4, 5 or 6. Preferred materials are those wherein R'' represents a divalent hydrocarbon group or a group R'''(NR'R''') wherein R''' represents a divalent hydrocarbon group, R' is as referred to above and s has a value in the range 0 to 4, more preferably 1 or 2. Preferred groups R''NXR' are according to the general formula

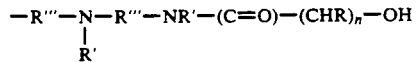

in which R''' is selected from the groups $-(CH_2)_2-$, $-(CH_2)_3-$, $-(CH_2)_4-$ and $-CH_2CH(CH_3)CH_2-$, and R' represents a hydrogen atom. The hydrolysable groups A of the silane (A) may be selected for example, from alkoxy, (e.g. methoxy, ethoxy or propoxy) alkoxyalkoxy (e.g. methoxy-ethoxy) acetoxy and halogen (e.g. chlorine). The silanes (A) are hydrolysable materials and may be employed as end-blocking units for polysiloxanes, or as chain extending or chain branching agents depending on the values of a and b. They may be hydrolysed to provide a polysiloxane with or without the presence of other silanes, for example to provide a polysiloxane (8), or condensed with for example polysiloxanes having hydroxyl or other reactive groups, for example linear α,ω dihydroxypolysiloxanes, to provide a polysiloxane (B). The polysiloxanes (B) comprise at least one, and preferably two or more, units according to the general formula (i). The polydiorganosiloxane (B) preferably also contains siloxane units according to the general formula (ii)

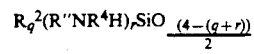

wherein $R^4$ represents a hydrogen atom, an alkyl group having 1 to 20 carbon atoms, an alkenyl group or an aryl group, q has the value 0, 1, 2 or 3 and r has the value 0, 1 or 2. R'' in this formula may represent R'''(NR'R''') as referred to above. Preferred polysiloxanes according to the invention include both siloxane units (ii) which have groups $R''NR^4H$ and siloxane units (ii) which have no groups $R''NR^4H$ Preferred polysiloxanes according to the invention have 90% or more, suitably more than 95% and preferably 97 to 99% of siloxane units (ii) according to the general formula

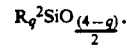

If desired, a polysiloxane according to the present invention may also comprise one or more siloxane units having other substituent groups, for example, oxyalkylene glycol groups. The groups $R^1$ and $R^2$ are preferably alkyl groups, the methyl group being the most preferred. Preferred polysiloxanes according to the invention are at least substantially linear materials, the most preferred being according to the average general formula

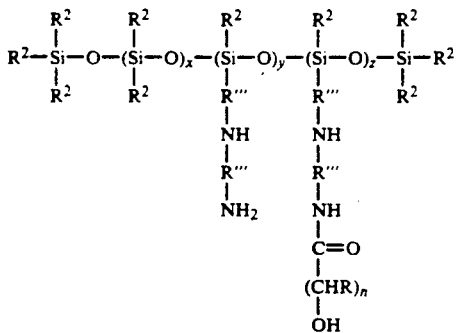

Preferred materials are those in which not less than 80% of the groups $R^2$ are methyl groups, x has a value from 20 to 1500, the ratio of y:z lies in the range 1:4 to 4:1 and the ratio z:x is less than 5:100.

Organosilicon compounds of the present invention may be prepared by reaction between a lactone and an organosilicon compound having an amino substituent. Suitable lactones have the formula

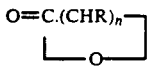

in which R represents a hydrogen atom or a hydrocarbon group having for example up to 7 carbon atoms, such as may be present when the lactone has been derived from a γ hydroxy acid and n has a value in the range 2 to 7. Preferred lactones are those in which each R represents a hydrogen atom and n has the value 3, g, 5 or 6, for example γ butyrolactone and epsilon caprolactone. Various amino substituted organosilicon compounds are known and available and they can be made by methods known in the art. The amino substituted organosilicon compound may be (A) a silane according to the general formula $R^1{}_aA_bSi(R''NR^4H)_c$ or (B) a polysiloxane having one or more siloxane units according to the general formula (iii)

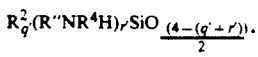

any remaining units of the polysiloxane being according to the general formula

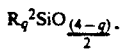

wherein A represents a hydroxyl group or a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, R" represents a divalent hydrocarbon group which may have nitrogen, oxygen or sulphur present in the carbon chain, a has the value 0, 1, or 2, b has the value 1, 2, or 3, c has the value 1 or 2, the sum of a+b+c=4, q has the value 0, 1, 2 or 3, q' has the value 0, 1, or 2, and r' has the value 1 or 2. The hydrolysable aminosilane may have hydrolysable groups selected for example, from alkoxy, alkoxyalkoxy, acetoxy and chloro. The alkoxy silanes are generally preferred. The amino substituted polysiloxanes may be prepared from precursors comprising one or more hydroxy polysiloxanes and hydrolysable aminosilanes.

Suitable hydroxy polysiloxanes include those in which the organo groups are at least predominantly alkyl groups having up to eight carbon atoms. When preparing an amino substituted polysiloxane intended for use in preparation of organosilicon compounds according to the invention, if desired, a silicone material capable of providing a desired degree of chain branching in the polysiloxane may be employed among the precursors for the amino substituted polysiloxane. Suitable materials are silanes $R'A_3Si$ and $A_4Si$. The amino substituted polysiloxane may be condensed and or equilibrated with selected organosilicon compounds of appropriate structure and molecular weight. Desirably the amino substituted polysiloxane has a major proportion of siloxane units of the general formula

and a minor proportion of siloxane units of the general formula

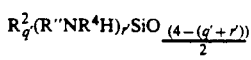

wherein $R^2$, R", $R^4$, q' and r' are as aforesaid. As mentioned above, examples of suitable groups R''' include —(CH$_2$)$_2$—, —(CH$_2$)$_3$—, —(CH$_2$)$_4$— and —CH$_2$CH(CH$_3$)CH$_2$—. Operative amino containing substituents R"NR$^4$H include —(CH$_2$)$_3$—NH$_2$, —(CH$_2$)$_3$NHCH$_2$CH$_2$NH$_2$, —CH$_2$CH(CH$_3$)CH$_2$NHCH$_2$CH$_2$NH$_2$, and —(CH$_2$)$_3$—NHCH$_2$CH$_2$NHCH$_2$CH$_2$NH$_2$. Preferred amino substituted polysiloxanes are those in which the $R^2$ groups are lower alkyl e.g. methyl groups or phenyl groups, and which have two or more amino siloxane units per molecule. Most preferred are those in which at east 80% of the groups $R^2$ are methyl groups.

The organosilicon compounds of the invention may be made by any convenient method, for example, by modification of some or all of the amino groups of the appropriate aminopolysiloxane or aminosilane. Silanes produced may be subsequently hydrolysed or condensed e.g. with a siloxane or polysiloxane or other silane in known manner, e.g. by emulsion polymerisation, to provide a polysiloxane. Similarly, polysiloxanes produced may be condensed with a siloxane, polysiloxane or silane in known manner. If desired the condensation step may be followed by equilibration and separation in known manner. Reaction between the lactone and the amino substituted organosilicon compound to form the amide may be carried out under a variety of conditions and is preferably carried out by heating the reactants together, optionally for example, in aqueous emulsion or in solution, most preferably under reflux in, for example, methyl ethyl ketone, toluene or ethanol. The proportions of the reactants employed may be chosen so that the desired proportion of the amino groups of the amino substituted organosilicon compound are converted to the amido form. For example one may ensure that from 20 to 80% of the primary amino groups are modified by reaction with the lactone.

The present invention provides in another of its aspects an organosilicon compound which comprises (A)

a silane according to the general formula $R^1{}_aA_b\text{-}Si(R''NXR')_c$ or (B) a polysiloxane comprising one or more siloxane units according to the general formula (i)

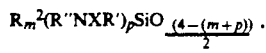

any remaining units of the polysiloxane being at east predominantly according to the general formula (ii)

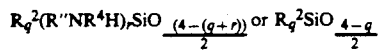

wherein A represents a hydroxyl or a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, $R'$ represents a group $R^4$ or a group $X$, $R''$ represents a divalent hydrocarbon group which may have nitrogen, oxygen or sulphur present in the carbon chain, $X$ represents a group $CO(CHR)_nOH$ in which R represents a hydrogen atom or an alkyl group, a has the value 0, 1, or 2, b has the value 1, 2, or 3, c has the value 1 or 2, the sum of $a+b+c=4$, m has the value 0, 1 or 2, p has the value 1 or 2, q has the value 0, 1, 2 or 3, r has the value 0, 1 or 2, and n has a value in the range 2 to 7.

The present invention provides in another of its aspects a method for the preparation of a polydiorganosiloxane having a group $=NCO(CHR)_nOH$ connected with a silicon atom of a siloxane unit of the polydiorganosiloxane wherein R represents a hydrogen atom or an alkyl group and n has a value in the range 2 to 7 which method comprises heating together under reflux conditions a lactone of the general formula

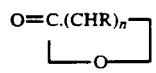

and an amino substituted polydiorganosiloxane composed of at least one unit according to the general formula

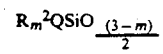

wherein $R^2$ represents a hydrogen atom or a hydrocarbon group having up to 8 carbon atoms, m has the value 0, 1 or 2 and Q represents —$R''NHR'$ or —$R''NR'R'''NHR'$ wherein $R'$ represents a hydrogen atom, an alkyl group having up to 20 carbon atoms, an alkenyl group or an aryl group, $R''$ and $R'''$ each represent a divalent hydrocarbon group which may have oxygen or sulphur in the carbon chain, and units according to the general formula

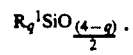

wherein $R^1$ represents a monovalent hydrocarbon group having up to 8 carbon atoms, and q has the value 0, 1, 2 or 3.

The invention provides in another of its aspects a method for the preparation of an organosilicon compound having a group $=NCO(CHR)_nOH$ connected with a silicon atom of the organosilicon compound wherein R represents a hydrogen atom or an alkyl group and n has a value in the range 2 to 7 which method comprises heating together under reflux conditions a lactone of the general formula

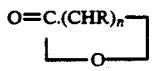

and an amino substituted organosilicon compound which comprises (A) a silane according to the general formula $R^1{}_aA_bSi(R''NR^4H)_c$ or (B) a polysiloxane having one or more siloxane units according to the general formula (iii)

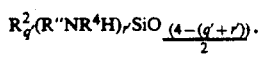

any remaining units of the polysiloxane being according to the general formula (iv)

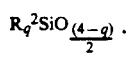

wherein A represents a hydroxyl or a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, $R''$ represents a divalent hydrocarbon group which may have nitrogen, oxygen or sulphur present in the carbon chain, a has the value 0, 1, or 2, b has the value 1, 2, or 3, c has the value 1 or 2, the sum of $a+b+c=4$, q has the value 0, 1, 2 or 3, q' has the value 0, 1, or 2, and r' has the value 1 or 2.

Organosilicon compounds according to the invention find use in a variety of applications for example as coatings or finishes on various substrates. They may be formulated for example, as solutions or emulsions and may be formulated so as to become cured on the substrate to which they have been applied. For example, they may be employed as a blend with other ingredients for example, polydimethylsiloxanes or with materials commonly employed in coatings or finishes. The organosilicon compounds are efficacious in the treatment of fibres and particularly natural fibres, for example new or freshly laundered textile fabrics consisting of or incorporating fibres of cotton, which may be blended with other fibres for example polyester, to provide a finish which confers a good handle or feeling of softness and a less yellow colouring to the fabric than similar treatments with the corresponding polysiloxane having solely amino organofunctionality. Those polysiloxanes according to the invention having both amido siloxane units as specified and primary amino substituted siloxane units may be used for the treatment of fibres and particularly natural fibres, for example textile fabrics incorporating fibres of cotton, to provide a finish which shows a desirable blend of softness, whiteness and durability. The preparation of organosilicon compounds of the invention from the appropriate lactone and silicon compound is particularly beneficial as no undesirable by-product is released during the reaction.

Preferred organosilicon compounds according to the invention which are intended for application in the form of an aqueous emulsion to fibres and fabrics are substantially linear materials. They may have a viscosity in excess of 50,000 but we prefer to employ materials having a viscosity of less than 50,000 mm²/s, more preferably less than 5000 mm²/s.

In order that the invention may become more clear there now follows a description of example organosilicon compounds which are illustrative of the invention. In the Examples all parts and percentages are expressed by weight unless otherwise specified, and Me signifies the methyl group.

EXAMPLE 1

253 7 parts (0.037 moles) of a polysiloxane of the average general formula $$Me_3SiO(Me_2SiO)_{195.5}(MeQSiO)_{4.5}SiMe_3$$

in which Q represents the group $CH_2.CHMe.CH_2.NH.(CH_2)_2NH_2$ (aminosioxane 1), 7 parts (0.0814 moles) γ butyrolactone $$\underset{\underset{O}{\rule{1cm}{0.4pt}}}{O=C.(CH_2)_3}$$

and 100 parts of toluene were heated at 80° C. for 5 hours under nitrogen, with constant stirring and reflux. The product was stripped of toluene using a rotary evaporator. The polysiloxane produced (Example polysiloxane 1) was a slightly yellow fluid having a viscosity of 2920 mm²/s at 25° C. Spectroscopic studies (NMR) showed the polymer contained amido groups and analysis of the nitrogen content of the polymer by acid titration showed that all primary amino groups of the polysiloxane had been converted. It was thus determined that Example polysiloxane 1 was of the formula $$Me_3SiO(Me_2SiO)_{195.5}(MeQ'SiO)_{4.5}SiMe_3$$

in which Q' represents the group $CH_2CHMeCH_2NH(CH_2)_2NHCO(CH_2)_3OH$.

EXAMPLE 2

172.7 parts (0.0222 moles) of aminosiloxane 1, 5.73 parts (0.0503 moles) epsilon caprolactone $$\underset{\underset{O}{\rule{1cm}{0.4pt}}}{O=C.(CH_2)_5}$$

and 00 parts toluene were heated at 80° C. for 5 hours under nitrogen, with constant stirring and reflux. The product was stripped of toluene using a rotary evaporator. The polysiloxane produced (Example polysiloxane 2) was a slightly yellow fluid having a viscosity of 11,100 mm²/s at 25° C. From spectroscopic studies (NMR) and analysis of the nitrogen content of the polymer it was determined that the Example polysiloxane 2 was of the formula $$Me_3SiO(Me_2SiO)_{195.5}(MeQ''SiO)_{4.5}SiMe_3$$

in which Q" represents the group $CH_2.CHMe.CH_2.NH.(CH_2)_2NHCO(CH_2)_5OH$.

EXAMPLE 3

489.3 parts (0.0630 moles) of a polysiloxane of the average general formula $$Me_3SiO(Me_2SiO)_{98}(MeQSiO)_2SiMe_3$$

in which Q represents the group $CH_2.CHMe.CH_2.NH.(CH_2)_2NH_2$ (aminosiloxane 2), and 13.1 parts (0.152 moles) γ butyrolactone were heated at 80° C. for 5 hours under nitrogen, with constant stirring and reflux. The polysiloxane produced (Example polysiloxane 3) had a viscosity of 922 mm²/s at 25° C. From spectroscopic studies (NMR) and analysis, it was determined that Example polysiloxane 3 was of the formula $$Me_3SiO(Me_2SiO)_{98}(MeQ'SiO)_2SiMe_3$$

in which Q' represents the group $CH_2.CHMe.CH_2.NH.(CH_2)_2NHCO(CH_2)_3OH$.

EXAMPLE 4

45.6 parts of a trimethylsilyl end-blocked polydimethylsiloxane, 1387.1 parts dimethyl cyclic siloxanes, 71.1 parts $(MegSiO)_4$ wherein g represents $CH_2CH(Me)CH_2NH(CH_2)_2NH_2$ and 9.2 parts potassium silanolate were heated at 150° C. under nitrogen for 5 hours. The product was then allowed to cool to 70° C. and 0.48 part glacial acetic acid was added to the product which was then stirred for a further hour at 70° C. It was then allowed to cool to room temperature and then filtered. The resulting clear colourless fluid had a viscosity of 150mm²/s. 1080.6 parts of this fluid and 28.7 parts of γ butyrolactone were heated at 80° C. under nitrogen for 5 hours. The resulting example polysiloxane 4 was a clear, slightly yellow, fluid having a viscosity of 1472 mm²/s and was of the average general formula $$Me_3SiO(Me_2SiO)_{98}(MeQ'SiO)_2SiMe_3$$

in which Q' represents the group $CH_2CHMeCH_2NH(CH_2)_2NHCO(CH_2)_3OH$.

EXAMPLE 5

Each of the Example polysiloxanes 1, 2, 3 and 4 was found capable of formulation as a solution or emulsion which when applied to a cotton fabric exhibited acceptable non-yellowing characteristics and conferred a soft handle to the fabric.

The performance of Example polysiloxane 3 as a fabric treating material was compared with that of an amino substituted polysiloxane based fabric finish in the following way. 15 parts of Example polysiloxane 3 were mixed with 9 parts of a non-ionic, ethoxy based surfactant, 0.25 part glacial acetic acid and 75.7 parts water and mixed to produce a first microemulsion. A second microemulsion was made up using 15 parts of an amino substituted polysiloxane C according to the average general formula $$Me_3(Me_2SiO)_{392}(MeQSiO)_8SiMe_3$$

in which Q represents the group $CH_2.CHMe.CH_2.NH.(CH_2)_2NH_2$, 9 parts of non-ionic, ethoxy based surfactant, 0.3 part glacial acetic acid, 0.2 part biocide and 75.5 parts water.

The microemulsions were used to provide first and second pad baths respectively, which were applied by padding to samples of woven cotton textile fabric. The cotton fabric as received had been treated with an optical brightening agent. The polysiloxanes were used in the padding baths in a concentration to provide 0.7% of the polysiloxane on the weight of the fabric. After removal from the pad bath the samples were heated for 2 minutes at 110° C. and then for 45 seconds at 170° C. The samples were aged for 24 hours and then assessed for whiteness and softness. Whiteness was judged by the human eye and by a Hunterlab tristimulus colorimeter system. In the accompanying Table 1, the higher numbers indicate greater whiteness; a difference of 2 or more is visible to the human eye and the results from the colorimeter were comparable with those from the human eye. Softness was evaluated by a panel of handle assesors on a scale of 0 to 10, with 10 being the softest; the average result is recorded in Table I.

TABLE I

|  | Whiteness | Softness |
|---|---|---|
| Sample from pad bath containing no polysiloxane | 111.3 | 0 |
| Sample from pad bath containing Example polysiloxane 3 | 107.3 | 10 |
| Sample from pad bath containing polysiloxane C | 105.6 | 9 |

EXAMPLE 6

Example silanes 1, 2, and 3 according to the invention were made as follows. Silane 1 was prepared thus: 1.63 moles of the silane Me.(MeO)$_2$SiQ in which Q represents the group CH$_2$.CHMe.CH$_2$.NH.(CH$_2$)$_2$NH$_2$ were charged to a split-necked flask fitted with reflux condenser, stirrer and thermometer. 1.63 moles γ butyrolactone

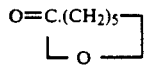

were added dropwise to the silane in the flask and the mixture stirred and heated to 80° C. The reacting mixture was maintained at this temperature under a blanket of nitrogen for five hours. The mixture was allowed to cool in the flask. The product was a viscous yellow liquid having a viscosity at 25° C. of 129,600 mm$^2$/s of the formula

Me.(MeO)$_2$SiCH$_2$.CHMe.CH$_2$.NH.(CH$_2$)$_2$NH-CO(CH$_2$)$_3$OH.

Silane 2 was prepared in the same manner as Silane 1 except that the group g of the aminosilane employed was (CH$_2$)$_3$.NH.(CH$_2$)$_2$NH$_2$. Silane 2 had a viscosity of 38,000 mm$^2$/s at 25° C. Silane 3 was prepared in similar fashion to Silane 1 except that the silane (MeO)$_3$SiQ in which g represents the group CH$_2$.CHMe.CH$_2$.NH.(CH$_2$)$_2$NH$_2$ was used as starting material. Silane 3 was a viscous yellow liquid having a viscosity of 43,280 mm$^2$/s at 25° C .

2 moles of Silane 1 was mixed with 1 mole of α,ω dihydroxypolydimethyl siloxanes having a viscosity of 150 mm$^2$/s, heated to 50° C. for four hours and then cooled to room temperature. An aqueous emulsion was prepared using this product together with an ethoxy based surfactant. The emulsion was padded onto a cotton fabric such that about 0.7% silicone solids was present on the weight of the fabric. The fabric was found to exhibit non-yellowing characteristics and to confer a soft handle to the fabric.

EXAMPLE 7

Example polysiloxanes 5, 6 and 7 were prepared according to the method described in Example g, except that the aminosiloxane and lactone were employed in proportions to convert 25%, 50% and 75% respectively of the primary amino groups present to groups =NCO(CHR)$_n$OH.

These polysiloxanes 5, 6 and 7 were according to the average general formula

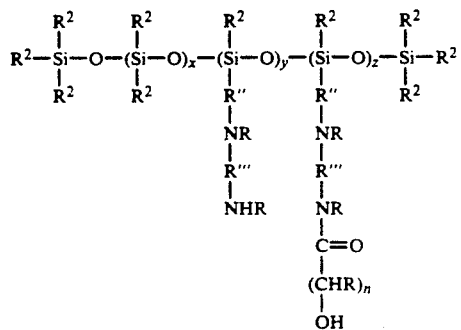

in which each R$^2$ represents a methyl group, each R represents a hydrogen atom, each R" represents —CH$_2$.CH(CH$_3$).CH$_2$—, each R''' represents —CH$_2$.CH$_2$— and n is 3, the siloxane units being in proportions such that the values of x, y and z were as shown in Table II.

TABLE II

| Example Polysiloxane | x | y | z | Ratio y:z |
|---|---|---|---|---|
| 5 | 98 | 1.5 | 0.5 | 3:1 |
| 6 | 98 | 1 | 1 | 1:1 |
| 7 | 98 | 0.5 | 1.5 | 1:3 |

EXAMPLE 8

Microemulsions were produced and their performance on woven cotton fabric was examined. The microemulsions were made up as described in Example 5 using polysiloxane C, aminosiloxane 1 and Example polysiloxanes 3, 4, 5, 6 and 7. The emulsions were padded onto woven cotton fabric and the softness of the fabric samples evaluated as described in Example 5. Softness of the samples was evaluated before and after five wash cycles and the durability of the treatment thus assessed. For this purpose, the samples were washed and dried according to International Standard 6330 washing procedures for horizontal drum machines type A1, Procedure No 6A and a tumble drier using 2 kg of samples and Persil washing powder. The results are shown in Table III.

TABLE III

| Poly-siloxane | y/z | Softness before washing | Softness after washing (5 cycles) |
|---|---|---|---|
| None | — | 0 | |
| C | — | 10 | 8 |
| 3 | | 10 | 4 |
| 4 | | 10 | 4 |
| 5 | 3 | 10 | 8 |

TABLE III-continued

| Poly-siloxane | y/z | Softness before washing | Softness after washing (5 cycles) |
|---|---|---|---|
| 6 | 1 | 10 | 8 |
| 7 | 0.33 | 10 | 6 |
| amino-siloxane | 1 | 10 | 8 |

As can be seen from Table III, whereas all the fabric samples showed a comparable level of softness prior to washing, the samples treated with polysiloxane having at least some primary amino siloxane units showed a better retention of their softness, samples treated with those polysiloxanes having a ratio y:z of 1:1 or 3:1 being the best in this respect.

EXAMPLE 9

Microemulsions were produced and their performance on woven cotton fabric was examined. The microemulsions were made up as described in Example 5 using Example polysiloxanes 3, 5, 6 and 7, aminosiloxane 2 and an aminopolysiloxane according to the general formula Me$_3$SiO(Me$_2$SiO)$_{98}$(MeSiBO)$_2$SiMe$_3$ wherein B represents CH$_2$.CHMe.CH$_2$NHCH$_2$CH$_2$NHCOCH$_3$ obtained by reaction of a portion of aminosiloxane 1 and sufficient acetic anhydride to convert all the primary amino groups of the aminosiloxane to amide groups.

The emulsions were padded onto woven cotton fabric to provide 1% by weight silicone solids on the fabric, and onto polyester cotton fabric (65/35) to provide 0.5% by weight silicone solids on the fabric. The treated cotton fabric samples were dried at 110° C. for 2 minutes and cured at 150° C. for 2 minutes. The polyester cotton fabric samples were dried at 110° C. for 1 minute and cured at 180° C. for 30 seconds. Softness of the samples was evaluated as described in Example 5 and the whiteness index of each sample was measured using the Hunterlab colorimeter system. The results for woven cotton samples are shown in Table IV and those for polyester cotton samples are shown in Table V.

TABLE IV

| Polysiloxane | Whiteness | Softness |
|---|---|---|
| None | 50.5 | 0 |
| Aminosiloxane 2 | 40.0 | 8.8 |
| Example 5 | 42.4 | 8.0 |
| Example 6 | 43.7 | 7.0 |
| Example 7 | 42.7 | 6.6 |
| Example 3 | 47.4 | 6.6 |
| Amidosiloxane D | 49.2 | 2.8 |

TABLE V

| Polysiloxane | Whiteness | Softness |
|---|---|---|
| None | 75.7 | 0.4 |
| Aminosiloxane 2 | 69.6 | 8.2 |
| Example 5 | 68.2 | 6.8 |
| Example 6 | 69.4 | 7.6 |
| Example 7 | 71.3 | 8.8 |
| Example 3 | 74.0 | 7.6 |
| Amidosiloxane D | 77.5 | 4.0 |

As can be seen from Tables IV and V the samples of cotton fabric treated with those polysiloxanes having at least some amidosiloxane units formed from reaction with a lactone as hereinbefore described (Example polysiloxanes 3, 5, 6 and 7) showed greater whiteness than samples treated with aminosiloxane 2 containing no such groups. The polyester-cotton samples indicate that not less than 50% of the primary amino groups should be converted via the lactone reaction to enable provision of fabrics having desirable whiteness and softness. Samples of both types of fabrics treated with the polysiloxanes according to the invention showed a much more acceptable softness compared with samples made using amidosiloxane D.

That which is claimed is:

1. An organosilicon compound which comprises a polysiloxane comprising one or more siloxane units according to the general formula (i) R$^2_m$(R"NXR')$_p$SiO$_{(4-(m+p))/2}$, and siloxane units according to the general formula (ii) R$^2_q$(R"NR$^4$H)$_r$SiO$_{(4-(q+r))/2}$ wherein R$^2$ represents a hydroxyl group, a monovalent hydrocarbon group having up to 8 carbon atoms, a group OR$^1$ or a group COR$^1$, R$^4$ represents a hydrogen atom, an alkyl group having 1 to 20 carbon atoms, an alkenyl group or an aryl group, R' represents a group R$^4$ or a group X, R" represents a divalent hydrocarbon group which may have nitrogen, sulfur or oxygen present in the carbon chain, X represents a group CO(CHR)$_n$OH in which R represents a hydrogen atom or an alkyl group, m has the value 0, 1 or 2, p has the value 1 or 2, q has the value 0, 1, 2 or 3, r has the value 0, 1 or 2, and n has a value in the range 2 to 7; with the proviso that, the polysiloxane includes both siloxane units (ii) which have groups R"NR$^4$H and siloxane units (ii) which have no groups R"NR$^4$H.

2. An organosilicon compound according to claim 1 wherein R" represents R'"(NR'R'")$_s$ wherein R'" represents a divalent hydrocarbon group and s has a value in the range of 0 to 4.

3. An organosilicon compound according to claim 2 wherein R'" is selected from the groups —(CH$_2$)$_2$—, —(CH$_2$)$_3$—, —(CH$_2$)$_4$— or —CH$_2$CH(CH$_3$)CH$_2$—.

4. A polysiloxane according to claim 1 of the average general formula

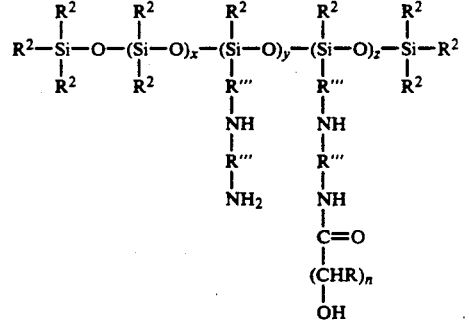

wherein R'" is selected from the groups —(CH$_2$)$_2$—, —(CH$_2$)$_3$—, —(CH$_2$)$_4$— or —CH$_2$CH(CH$_3$)CH$_2$—, not less than 80% of the groups R$^2$ are methyl groups, x has an average value from 20 to 1500, y has an average value from 0 to 50 and z has an average value from 0.5 to 50.

5. A polysiloxane according to claim 4 wherein $R_2$ is $CH_3$, R is H and y:z lies in the range 1:4 to 4:1.

6. A polysiloxane according to claim 4 wherein the ratio z:x is less than 5:100.

7. A method for the preparation of an organosilicon compound of claim 1 which method comprises heating together under reflux conditions a lactone of the general formula

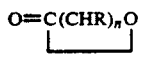

wherein R represents a hydrogen atom or an alkyl group and n has a value in the range 2 to 7 and (A) a silane according to the general formula $R^1{}_aA_b\text{-}Si(R''NR^4H)_c$ so that some, but not all, of the amino groups are converted to amido groups and hydrolyzing or condensing the silane produced to provide said organosilicon compound; or (B) a polysiloxane having one or more siloxane units according to the general formula (iii) $R^2{}_{q'}(R''NR^4H)_{r'}SiO_{(4-q'-r')/2}$, any remaining siloxane units of the polysiloxane being according to the general formula (iv) $R^2{}_qSiO_{(4-q)/2}$ so that some, but not all, of the amino groups are converted to amido groups wherein A represents a hydrolysable group, $R^1$ represents a monovalent hydrocarbon group having up to 8 carbon atoms, $R^2$ represents a hydroxyl group, a group $R^1$, a group $OR^1$ or a group $COR^1$, $R^4$ represents a hydrogen atom, an alkyl group having 1 to 20 carbon atoms, an alkenyl group or an aryl group, R'' represents a divalent hydrocarbon group which may have oxygen, nitrogen or sulfur in the carbon chain, a has the value 0, 1 or 2, b has the value 1, 2 or 3, c has the value 1 or 2, the sum of $a+b+c=4$, q has the value 0, 1, 2, or 3, q' has the value 0, 1, or 2, and r' has the value 1 or 2.

8. A method according to claim 7 wherein the lactone is γ butyrolactone or epsilon caprolactone.

9. A method according to claim 7 wherein $R^4$ represents a hydrogen atom and R'' represents, $-(CH_2)_3NHCH_2CH_2-$, $-CH_2CH(CH_3)CH_2NHCH_2CH_2-$ or $-(CH_2)_3NHCH_2CH_2NHCH_2CH_2-$.

10. A method according to claim 7 wherein the amino substituted polysiloxane used comprises up to 5 percent siloxane units according to the general formula (III).

11. A method according to claim 7 wherein all the primary amino groups of the amino substituted organosilicon compound are reacted with the lactone.

12. A fabric treating material in the form of an aqueous emulsion comprising a polydiorganosiloxane according to claim 1.

13. A fabric treating material in the form of an aqueous emulsion comprising a polydiorganosiloxane according to claim 7.

* * * * *